United States Patent [19]
Gellert

[11] Patent Number: 5,501,650
[45] Date of Patent: Mar. 26, 1996

[54] AUTOMATED MASTURBATORY DEVICE

[76] Inventor: Reinhard R. Gellert, 2821 N. Elm La., Arlington Heights, Ill. 60004

[21] Appl. No.: 118,154

[22] Filed: Sep. 8, 1993

[51] Int. Cl.⁶ ..................................................... A61F 5/00
[52] U.S. Cl. ................................................................. 600/38
[58] Field of Search ................ 600/38–41; 128/897–899

[56] References Cited

U.S. PATENT DOCUMENTS

| | | | |
|---|---|---|---|
| 4,407,275 | 10/1983 | Schroeder | 600/38 |
| 4,720,296 | 12/1988 | Segal | 600/38 |
| 5,244,453 | 9/1993 | Osbon et al. | 600/38 |

FOREIGN PATENT DOCUMENTS 154651  10/1932  Switzerland ............................. 600/41

*Primary Examiner*—Angela D. Sykes
*Assistant Examiner*—J. Lacyk

[57] ABSTRACT

A variable speed motor powering a crankshaft driven sealed transducer producing pneumatically induced reciprocating motion of a receiver when a male organ is inserted. The present invention employs a hermetic system to prevent loss of synchronization. The receiver is designed with an inner liner compliant enough to accommodate a plurality of sizes and shapes of male penises. The present invention produces a stroke of approximately 3 inches at a frequency of up to 350 per minute.

6 Claims, 4 Drawing Sheets

AUTOMATED MASTURBATORY DEVICE

BACKGROUND OF INVENTION

1. Field of Invention

This invention relates to male sexual aids, specifically mechanized sexual aids.

2. Description of Prior Art

Modern life today presents many new problems to human sexuality. First and foremost we are faced with a plague of unparalleled proportions known as AIDS. In addition there are many sexually transmitted viral and parasitic diseases which until recently were not widely recognized. Diseases such as Herpes II, genital warts, trichomoniasis, chlamydia, etc. Bacterial diseases like syphilis and gonorrhea have become resistant to antibiotics. The current economic downturn and the increase of multiple income families have all had an adverse effect on male and female sexuality. If men do not receive frequent enough sexual satisfaction, it usually leads to behavioral problems. These certainly include practicing unsafe sex, infidelity, and sexual abuse of women and children. It is the aim of the present invention to substantially improve male sexual satisfaction.

Artificial vaginas known in slang as "pocket pussies" exist in many styles. Penis enlarging pumps, erection maintainers, and male vibrators are all readily available. They can be goren at adult book and novelty stores. There is an enormous worldwide direct mail industry supplying adult video tapes and "adult sex toys". The majority of these products sold during 1993 for less than $70.00. A premium female sexual stimulator made by Abco Research of Monticello, Ill. retails for $1400.00. It is called the Sybian. The present invention is also a premium product. The present invention accurately simulates actual intercourse. It is self-powered and functions "hands off". This product is used to satisfy male sexual urge, but also has general therapeutic use. Its pneumatic design allows initiation to occur while the penis is flaccid. Men suffering from impotence, either circulatory or physiological in origin, will benefit. It is expected that urology clinics, fertility clinics, and sperm banks will also employ the present invention.

The principal prior art is described by U.S. Pat. No. 43,910,262 dated Oct. 7, 1975 by inventor Dan T. Stoughton. This was a therapeutic apparatus intended for producing orgasms in males and females. It contained a motor driven hydraulic actuator which produced positive and negative pneumatic pressure pulses. These pressure reversals produced reciprocating motion of a sleeve massaging a man's penis. The massaging sleeve was molded from clear vinyl. A principal flaw of this design is that it is impossible to hermetically seal a piston sliding within a cylinder. Because greater force is required for this sleeve to slide onto a penis than to slide off, the average pneumatic pressure is negative. Leakage past the cylinder seals will increase the working volume and cause the massaging sleeve to eventually fall off the man's penis. To overcome this problem, the designer required the use of a check valve 56, a manually adjustable needle valve 58, and a spring loaded valve 62. Also, because the massaging sleeve was made from vinyl, it was not capable of accommodating more than ⅛" variation in penis diameter. This design flaw required them to manufacture massaging sleeves in 8 sizes. The purchaser measured his erect penis before ordering one. Motor 14 of FIG. 1 looks just like a windshield wiper motor used in American automobiles in the early 1970's. Their maximum speed is about 100 rpm's at 12 volts direct current.

This patent eventually produced a commercial product known as the Accujac. It is no surprise that its maximum rated speed specified in its literature is 100 rpm's. Vigorous masturbation approaches 180 strokes per minute. The Accujac was very underpowered. Another major flaw in the design of the Accujac is that semen and lubricant always got into flexible tube 52. It enjoyed modest commercial success and was last produced circa 1985. The product retailed for $199.50 for the lowest cost version, and $895. for the "top of the line" model. The massaging sleeve was made to order in eight diameters and six shapes. In apparatus U.S. Pat. No. 4,312,350 titled "Apparatus for Collecting Seminal Fluids" dated Jan. 26, 1982 by Rosetta C. Doan I cite the following flaws: (1) The opening of the apparatus consisting of rim 25 and compression ring 70a and 70b is incapable of the resiliency required to seal or accommodate differences in organ size. (2) Reference column 5, paragraph 1, beginning "With reference now . . . " This paragraph describes actual use of the unit. It explains that the machine must be hand held. The operator must guide the animal penis into the unit and in contact with sphincter 32 and cone 30. (3) Observe the design of sleeves 27 and 28 with spring 26 in between. Sleeve 27 is not shown or implied to be a bellows capable of resisting collapse under vacuum. I must conclude that sleeve 27 would collapse subsequently vacuum wrapping spring 26. This will prevent spring retraction. I must conclude that this invention was never reduced to practice.

SUMMARY

The goal of this invention is to produce intense stimulation for any user. It is designed to create orgasms in 30 seconds or less, if desired. A successful design should be simple, easy to use, and easy to clean. The present invention meets all of the above requirements. The receiver cap is easily removable, and the receiver inner liner will clean up in seconds. Needle valves, check valves, pressure relief valves, and pulsators have all been eliminated. Bodily fluids are prevented from entering hoses by the hermetic design of the present invention. The receiver is lightweight and can be used in any position without it falling off.

DESCRIPTION OF PREFERRED EMBODIMENTS (AMENDED)

Figure 1:
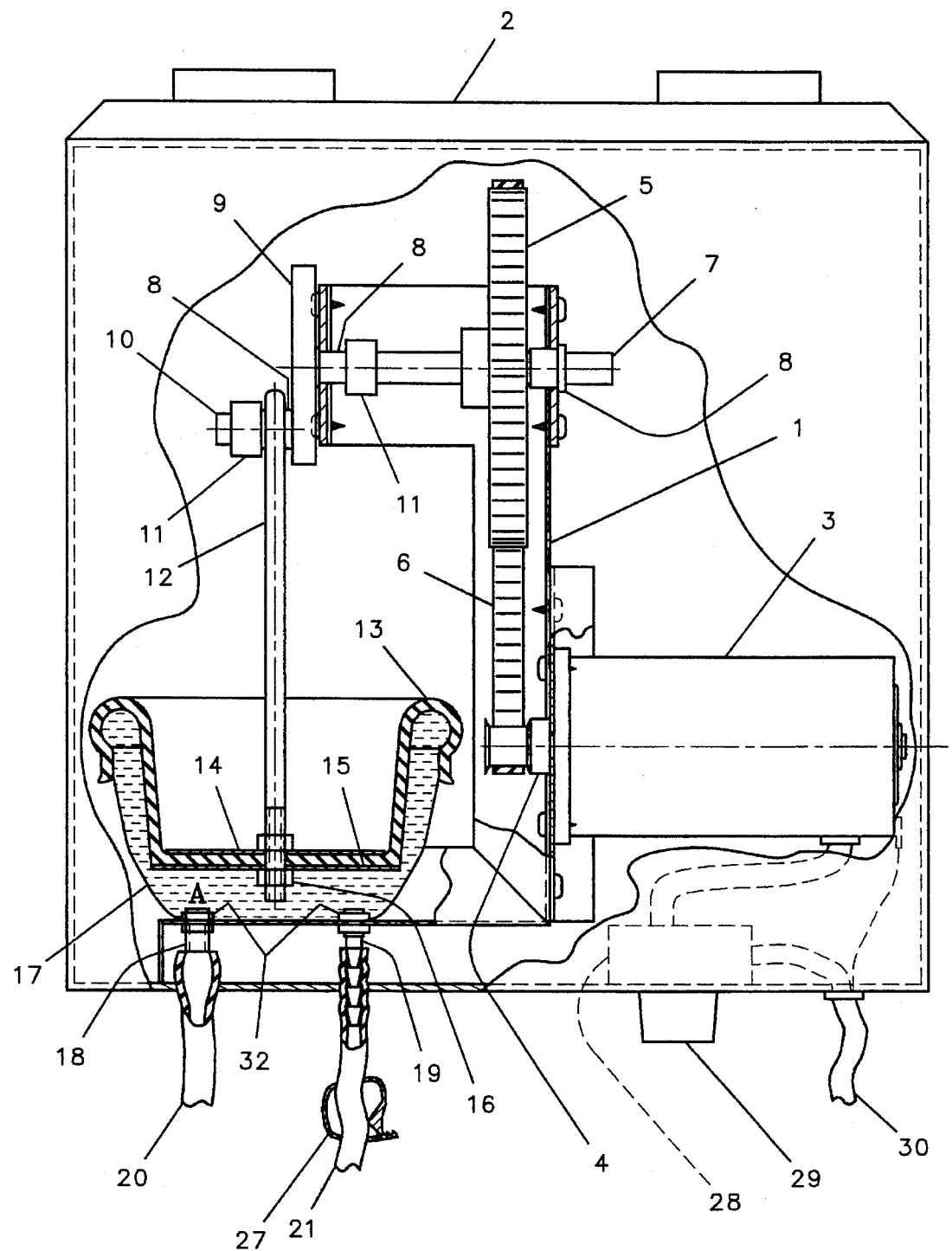
FIG. 1 is top view of the unit without the receiver.

The apparatus shown in FIG. 1 includes frame 10 made from inexpensive commercial quality sheet metal. The sheet metal is 18 gauge with zinc dichromate plating. It holds together all the components of the unit. This frame is attached to cover 12. Cover 12 is 18 gauge sheet metal plated with zinc dichromate. It is then painted with a catalyzed paint and silk screened with instructions for use and appropriate safety warnings. Frame 10 and cover 12 are attached to one another with five #10 sheet metal screws. Cover 12 fits inside of a doublewall molded case (not shown on the drawings), which has slots to receive cover 12. The case is a standard polyethylene blowmolded product. It is approximately 13 inches by 21 inches by 6½ inches outside dimension. Cover 12 is retained in slots and is secured in the case by four #12 screws. Means for providing reciprocating motion include motor 14. It is a one twentieth horsepower 90 volt direct current motor. Motor 14 and electronic speed control 68 constitute a variable speed controlled motor. Motor 14 has driving pulley 16 attached to its shaft. Timing belt 20 transmits force from driving pulley 16 to driven pulley 18. This drive system is a standard three millimeter pitch utilizing a timing belt nine millimeters wide. Driving pulley 16, driven pulley 18, and timing belt 20 comprise the speed reducing drive. Its ratio is 8 to 1. Pulley 18 is permanently attached to shaft 22 which rotates in bushings 24 and is held in place by shaft collar 30. Shaft collar 30 prevents axial displacement of shaft 22. Crank 26 is pressed on the end of shaft 22. Crankpin 28 is pressed in crank 26. Both shaft 22 and crankpin 28 are made from high quality case hardened and precision ground steel. The crankshaft assembly consists of shaft 22, crank 26, and crankpin 28. A sealed transducer assembly comprising a rolling diaphragm 34, a cup 44 serving as a chamber, and a connecting rod 32 attaching rolling diaphragm to the crankshaft. Connecting rod 32 translates the circular motion of crank pin 28 to reciprocating motion. Connecting rod 32 transmits this reciprocating motion to diaphragm 34. Bushing 24 is pressed into eyelet of connecting rod 32. Connecting rod 32 is prevented from sliding off crankpin 28 by shaft collar 30. Connecting rod 32 is attached to rolling diaphragm 34, using washers 38 and 40 and nuts 42. The penetration point of diaphragm 34 is sealed by a sealant, preventing air from escaping cup 44 during operation. Rolling diaphragm 34 is molded from gum rubber of 40 durometer and is between 0.160 to 0.240 inch wall thickness. It may be molded from other flexible and resilient material. Acceptable durometer is in the range of 40 to 80. It is designed for long life and acceptance of fluid pulses of up to +/-5 PSIG. The open end of rolling diaphragm 34 is attached to the open end of cup 44 by stainless steel hose clamp 36. This is a means for providing a sealed connection between the chamber and the diaphragm. Cup 44 has 2 holes on the bottom. These holes accept fittings 46 and 48. Cup 44 and frame 10 are attached by nuts 50. Penetration points in cup 44 are sealed to prevent leakage. A sealed transducer assembly consists of connecting rod 32, rolling diaphragm 34, stainless steel hose clamp 36, washer 38, washer 40, nuts 42, cup 44, fittings 46 and 48, and nuts 50. Fluid communication conduit 52 and rubber hose 54 are attached to firings 46 and 48 respectively and are three feet long each. The other end of the conduit 52 is attached to the receiver shown in FIGS. 3a and 3b. Clamp 66 is placed near the open end of hose 54.

Figure 2:
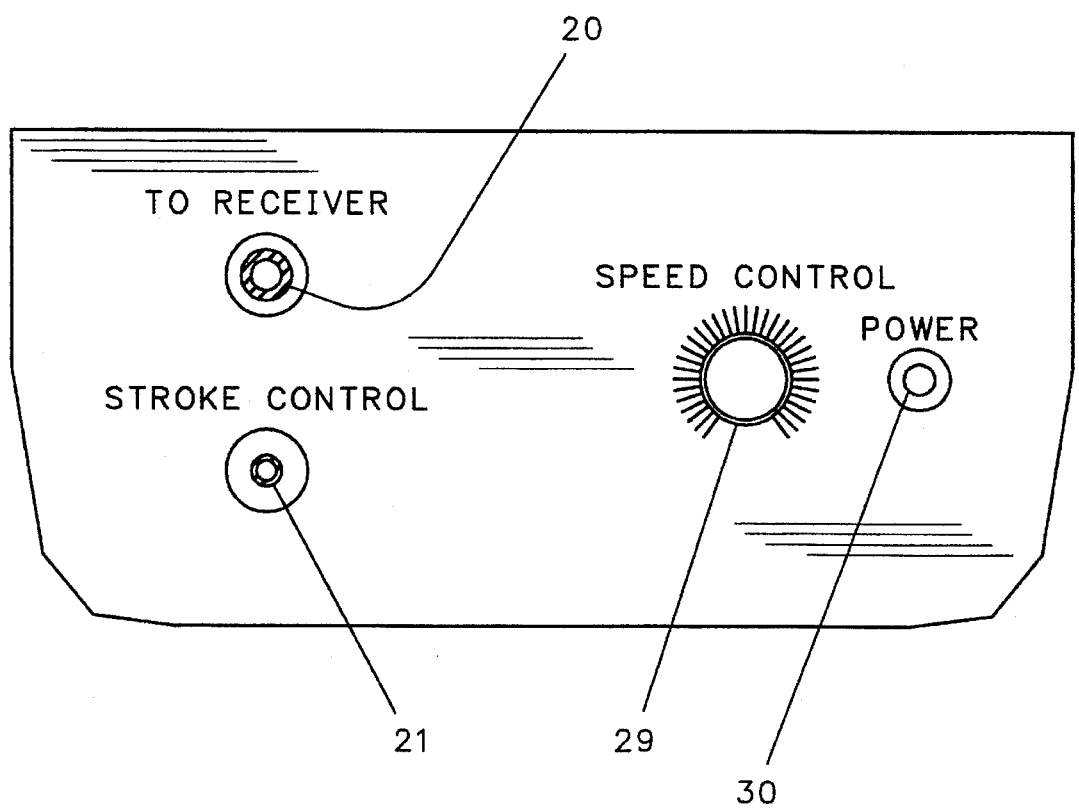
FIG. 2 is the view of the control panel.

FIG. 2 shows controls which are placed on the vertical side of cover 12. Conduit 52 and hose 54 shown in cross section are attached to fittings 46 and 48 through openings in the panel marked "TO RECEIVER" and "STROKE CONTROL". Power cord 72 supplies alternating current at 115 volts to the electronic speed control. The electronic speed control 68 furnishes direct current at selectively reduced voltage to motor 14. Knob 70 attaches to the electronic speed control potentiometer. All electrical components are grounded to frame 10 and through ground wire of cord 72.

Figure 3A:
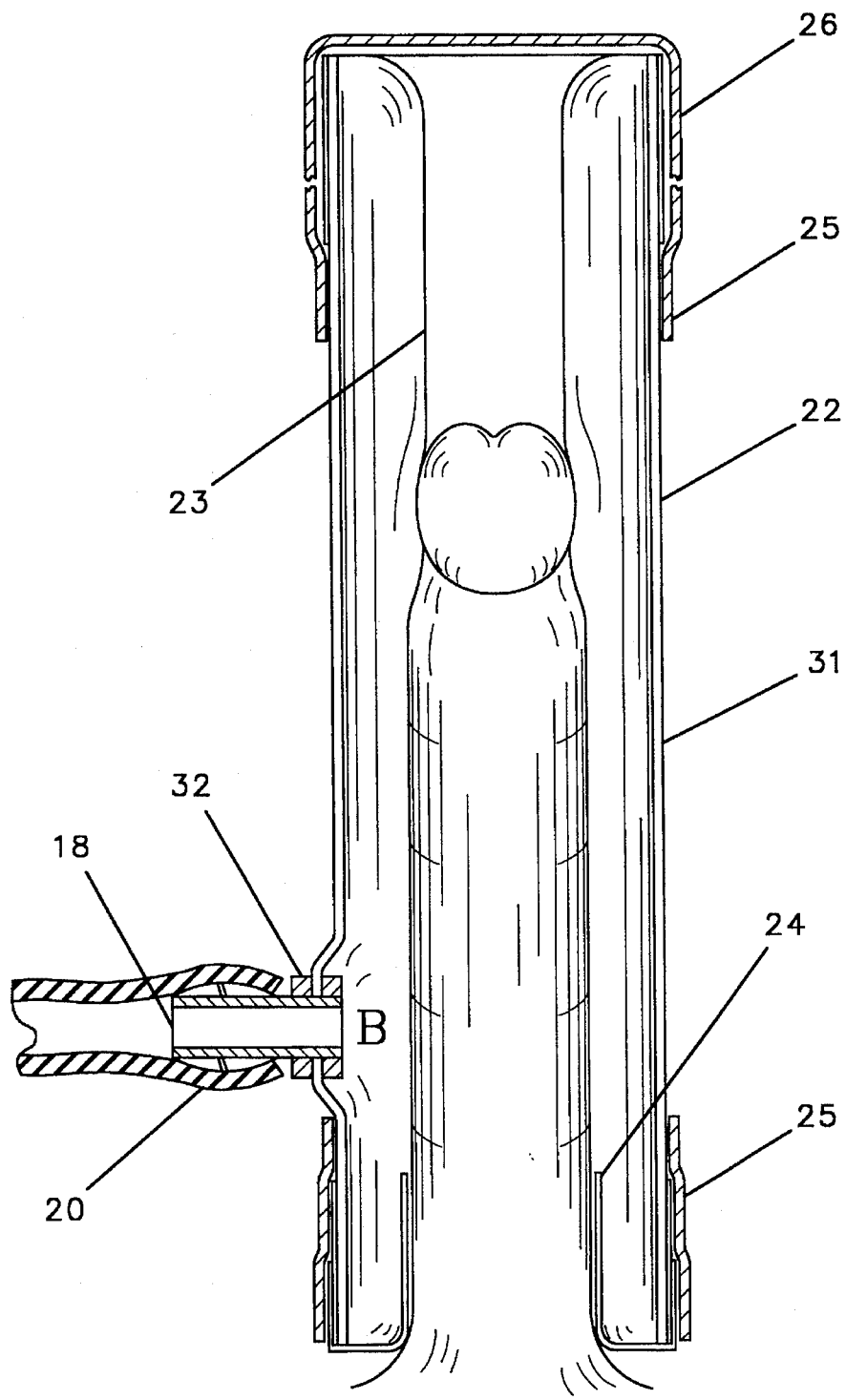
FIG 3a is the receiver under vacuum.
Figure 3B:
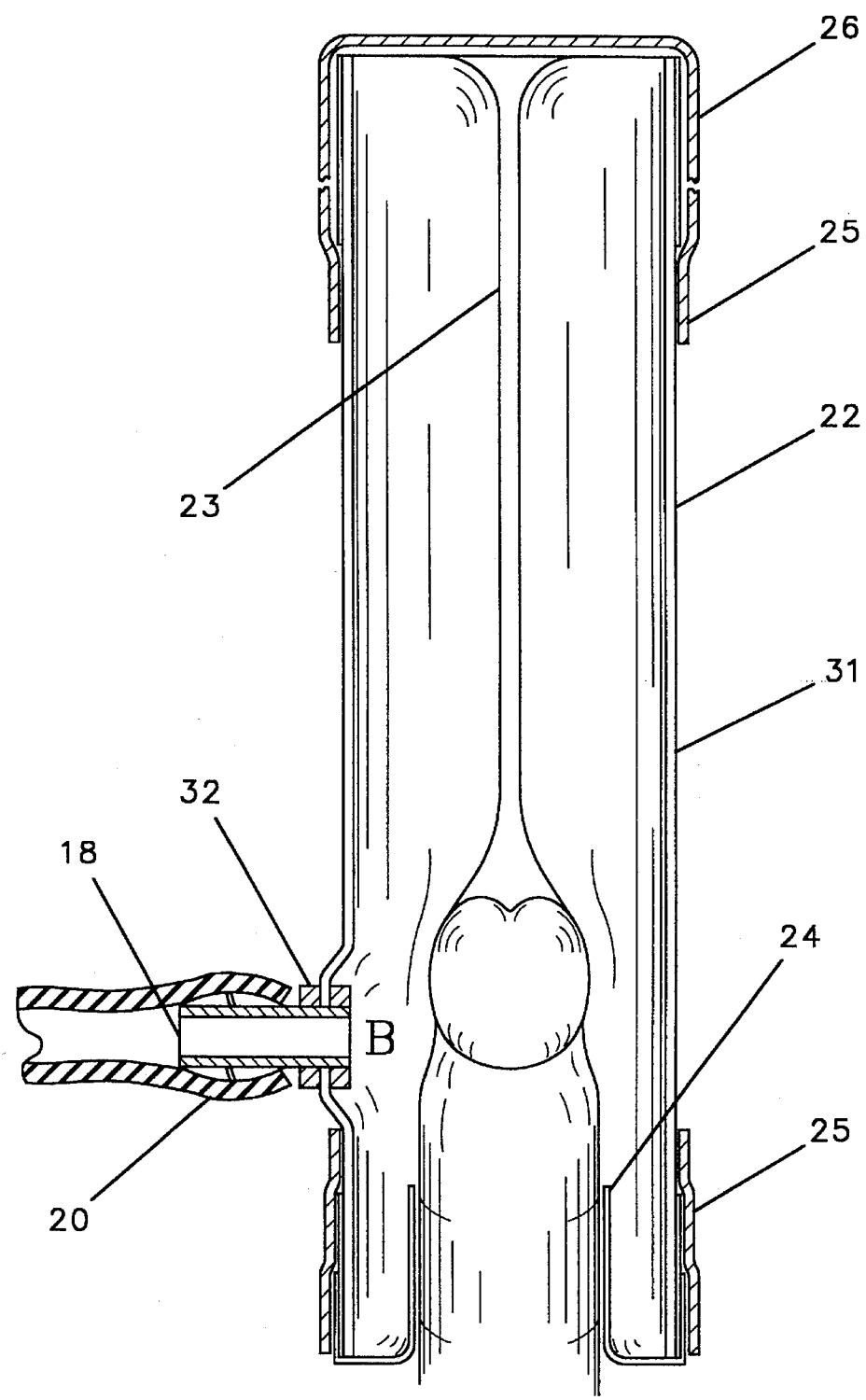
FIG. 3b is the receiver under pressure.

FIG. 3a and 3b show a generally hollow cylindrical receiver 74 under vacuum and under pressure, respectively. Receiver 74 comprises an elongated rigid tubular body made of clear plastic extruded tube 56, a pliable tubular liner made of rubber tube 58, rubber constrictor 60, vinyl sleeves 62, and removable vinyl cap 64. Clear plastic extruded tube 56 is approximately 2 inches inside diameter, 0.062 inches wall thickness, and 8 inches long. Clear plastic extruded tube 56 is thermally deformed to produce a flat area ¾" diameter. This flat is punctured to accept fitting 46. Rubber tube 58 is approximately 1,25" inside diameter by 0.030 wall thickness. This is commercially available extruded tubing. Rubber constrictor 60 is similar to 58 but has higher rubber content. Rubber constrictor 60 is about 2.5" long. One end of rubber constrictor 60 is folded about 1" over the open end of tube 56. Each end of rubber tube 58 is folded over clear plastic extruded tube 56. Together these two components form a pliable elongated annular bladder. Clear plastic extruded tube 56 has a fitting 46 attached to it at the proximal end by nuts 50, and the attachment between clear plastic extruded tube 56 and fitting 46 and nuts 50 is tightly sealed. Conduit 52 is detachable from fitting 46. Vinyl sleeves 62 are decorative, but also help to secure the ends of rubber tube 58. Removable vinyl cap 64 seals the [end furthest from fitting] distal end (furthest from fitting) 46.

THEORY OF OPERATION

The male sexual stimulator must be plugged into a 115 volt alternating current wall outlet. The inner liner (rubber tube 58) of receiver 74 is then generously lubricated. A gel type lubricant like K-Y brand is preferred. A thinner, less viscous lubricant may be used but will cause a longer stroke length if the coefficient of friction is reduced. Anyone with basic knowledge in the art will understand that if two pneumatic or hydraulic cylinders are properly attached and synchronized they can be made to transmit pneumatic or hydraulic force to each other. When the rod of the first cylinder is pushed in, it will cause the extended rod of the second cylinder to retract. It is also well known that leakage past the cylinder seals will cause synchronization to be lost. Many systems have been designed to solve loss of synchronization due to leakage past piston seals. Rephasing ports, needle valves, check valves, bypass valves, pressure relief valves, and pulsators have all been used to get around this problem. What is not apparent in the prior art is that eliminating the pneumatic piston seal also solves the synchronization problem. The reason for this inobviousness is that previous normally constructed diaphragms are unable to tolerate pressure reversals. Normal diaphragms tend to be thin rubber coated reinforcing material. It will produce noise when subject to pressure reversal because of popping. Rolling diaphragm 34 by design has internal stresses due to pressure differential. Its shape is relatively immune to pressure reversal and therefore is quiet during operation. Bellows are not able to meet the simultaneous requirements of volumetric efficiency, cost, pressure, and life cycle required for the present invention. By way of analogy the sealed transducer is equal to a driving cylinder; the receiver 74 with penis inserted is equal to the driven cylinder. In much the same way as the example of the cylinders, when the rolling diaphragm 34 of the hermetic-pneumatic-transducer is pushed into cup 44, it forces air into receiver 74 substantially displacing the penis that was fully inserted. The actual form of receiver 74 may be compared to a plunger cylinder where the penis is equal to a stationary plunger, the constrictor 60 is equal to the cylinder seal, and clear plastic extruded tube 56 is equal to the cylinder wall. Opening clamp 66 on rubber hose 54 permits the user to admit or withdraw air. This allows the user to fully collapse the inner liner, rubber tube 58, prior to inserting the penis. He may then synchronize the transducer to receiver by admitting or withdrawing air causing it to reciprocate on the penis without falling off or creating uncomfortable suction. The user then closes clamp 66 and the male sexual stimulator will continue its present operation as long as desired without loss of the present setting. Displacement of the inner liner is limited by the length times cross sectional area in the normally relaxed position. The suction force acting on the transducer rapidly increases as the inner rubber stretches. If the rubber constrictor is stretched larger than the inserted penis, the hermetic seal between the penis and constrictor is lost. Air will fill the unused collapsed portion of the inner liner. This causes the penis to be expelled on the next stroke. The constrictor and liner in the relaxed position prevents this because it is of a smaller diameter than a small penis in the normal range. It is typically 1.187" inside diameter. The constrictor and inner liner may be stretched to a diameter between 1.625" and 1.750" and still maintain forces low enough for proper operation. Stroke length of the present invention varies between two inches and four and a half inches depending upon conditions of use. The operator will turn knob 70 to adjust the voltage output of electronic speed control 68 which then controls the speed of motor 14. As previously inferred, motor 14 powers a timing belt drive. The present invention uses an 8:1 reduction ratio. This rotates a crankshaft which when coupled to the connecting rod 32 of the sealed transducer produces reciprocating pneumatic energy to be transmitted to receiver 74. The present invention may be adjusted from less than 30 strokes per minute to more than 350 strokes per minute. The inner pliable liner (rubber tube 58) prevents bodily fluids or lubricant from ever entering the hermetically sealed space, defined as area A of FIG. 1, area B of FIGS. 3, Conduit 52 and hose 54. Vinyl cap 64 is easily removable from clear plastic extruded tube 56. This feature provided for convenient cleaning of the interior portion of rubber tube 58 after use.

While this invention has been particularly shown and described with reference to the above, it will be understood by those skilled in the art that various changes in form and detail may be made without departing from the spirit and the scope of the invention.

The embodiments of the invention in which an exclusive property or privilege exists are claimed and defined as;

1. An automated masturbatory device comprising:
   (a) means for providing reciprocating motion;
   (b) a sealed transducer having fluid therein and a fitting thereon for fluid communication;
   (c) a connecting rod;
   (d) a fluid communication conduit;
   (e) a generally hollow cylindrical receiver including:
      (1) a pliable elongated annular bladder positioned therein;
      (2) the annular bladder having a fitting thereon for connection to said fluid communication conduit;
      (3) a removable cap;
   (f) said means for providing reciprocating motion being connected to said sealed transducer with said connecting rod; said sealed transducer provides repeated fluid pulses to the receiver via said fluid communication conduit; said repeated fluid pulses acting on the receiver with said removable cap installed cause masturbatory motion when said receiver is placed over a male penis.

2. The automated masturbatory device of claim 1 wherein: said means for providing reciprocating motion includes an electric motor being in driven relation with a crankshaft and said connecting rod.

3. The automated masturbatory device of claim 2 wherein: said means for providing reciprocating motion include means for varying the speed of rotation of said electric motor.

4. The automated masturbatory device of claim 1 wherein:
   (a) the transducer comprising:
      (1) a chamber having fluid therein;
      (2) a rolling diaphragm received on said chamber;
      (3) means for providing a sealed connection between said chamber and the diaphragm;
   (b) the rolling diaphragm comprising:
      (1) a stiff disk and:
      (2) a pliable wall surrounding said disk, whereby said diaphragm withstands reversals of predetermined fluid pressure and buckling forces and:
   (c) the transducer connected to said means for providing reciprocating motion by said connecting rod produces fluid pulses transmitted via said fluid communication conduit to the receiver.

5. The automated masturbatory device of claim 1 wherein: said fluid communication from said sealed transducer through the conduit to the receiver is unimpeded in either direction.

6. An automated masturbatory device comprising:
   (a) means for providing repeated fluid pulses and:
   (b) a receiver comprising:
      (1) a rigid tubular body having a proximal and distal end;
      (2) a pliable tubular liner therein, said rigid tubular body and said pliable tubular liner forming an annular bladder, and said annular bladder having a fitting for connection to said means for providing repeated fluid pulses, and;
      (3) a removable cap, said removable cap fixably positioned on the distal end of said annular bladder, whereby fluid pulses in said receiver cause masturbatory motion when said receiver is placed over a male penis.

* * * * *